United States Patent
Oh et al.

(10) Patent No.: US 9,014,455 B2
(45) Date of Patent: Apr. 21, 2015

(54) X-RAY IMAGING APPARATUS AND X-RAY IMAGE GENERATING METHOD

(71) Applicants: Samsung Electronics Co., Ltd., Suwon-si (KR); Samsung Life Public Welfare Foundation, Seoul (KR)

(72) Inventors: Hyun-Hwa Oh, Hwaseong-si (KR); Kang-Eui Lee, Seoul (KR); Seo-Young Choi, Seoul (KR); Young-Hun Sung, Hwaseong-si (KR); Myung-Jin Chung, Seoul (KR)

(73) Assignees: Samsung Electronics Co., Ltd., Suwon-si (KR); Samsung Life Public Welfare Foundation, Seoul (KR)

( * ) Notice: Subject to any disclaimer, the term of this patent is extended or adjusted under 35 U.S.C. 154(b) by 90 days.

(21) Appl. No.: 13/948,832

(22) Filed: Jul. 23, 2013

(65) Prior Publication Data
US 2014/0119507 A1 May 1, 2014

(30) Foreign Application Priority Data

Oct. 30, 2012 (KR) .......................... 10-2012-0121577
Mar. 28, 2013 (KR) .......................... 10-2013-0033895

(51) Int. Cl.
*G06K 9/00* (2006.01)
*A61B 6/00* (2006.01)

(52) U.S. Cl.
CPC ........................................ *A61B 6/52* (2013.01)

(58) Field of Classification Search
CPC ......... A61B 6/482; H04N 5/3205; G06T 5/50
USPC ............ 382/130, 132; 378/98.9, 98.11, 98.12
See application file for complete search history.

(56) References Cited

U.S. PATENT DOCUMENTS 8,442,289 B2 * 5/2013 Kadomura et al. ........... 382/128
8,654,921 B2   2/2014 Cho

FOREIGN PATENT DOCUMENTS

| JP | 2009-178493 A | 8/2009 |
|---|---|---|
| KR | 10-2011-0032047 A | 3/2011 |
| KR | 10-2011-0115762 A | 10/2011 |
| KR | 10-2012-0055174 A | 5/2012 |

* cited by examiner

*Primary Examiner* — Jurie Yun
(74) *Attorney, Agent, or Firm* — Sughrue Mion, PLLC

(57) ABSTRACT

Disclosed herein are an X-ray imaging apparatus and an X-ray image generating method in which constituent materials of a target object are separated and mapped to different colors in order to provide one image which has improved distinction between tissues. The X-ray imaging apparatus includes an X-ray generator which generates X-rays and irradiates the X-rays toward a target object, an X-ray detector which acquires X-ray data which corresponds to a plurality of energy bands by detecting X-rays which have passed through the target object, and a controller which acquires a plurality of material images in which a plurality of materials constituting the target object are respectively displayed and brightness information from the X-ray data, generates one image by mapping different color channels to the plurality of material images and combining the plurality material images into a single image, and applying the brightness information to the generated image.

16 Claims, 15 Drawing Sheets

X-RAY IMAGING APPARATUS AND X-RAY IMAGE GENERATING METHOD

CROSS-REFERENCE TO RELATED APPLICATIONS

This application claims priority from both of Korean Patent Application No. 10-2012-0121577, filed on Oct. 30, 2012, and Korean Patent Application No. 10-2013-0033895, filed on Mar. 28, 2013, in the Korean Intellectual Property Office, the disclosures of which are incorporated herein by reference in their entireties.

BACKGROUND

1. Field

Exemplary embodiments relate to an X-ray imaging apparatus which generates an X-ray image by causing X-rays of multiple energy bands to penetrate a target object and an X-ray image generating method.

2. Description of the Related Art

An X-ray imaging apparatus detects the internal structure of a target object by irradiating X-rays toward the target object and analyzing X-rays which have passed through the target object. Since X-ray transmittance varies based on characteristics of materials constituting the target object, the internal structure of the target object may be imaged by detecting the intensity of the X-rays which have passed through the target object.

Conventionally, an X-ray image is obtained mainly by irradiating X-rays of a single energy. However, in this case, a distinction between a calcifying nodule and a non-calcifying nodule or a distinction between a region in which fine tissues are overlapped and a nodule may be difficult to discern.

Therefore, a method for separating constituent materials of a target object from a plurality of X-ray images which correspond to different energy bands has been developed, and various researches on such a method are underway.

SUMMARY

Therefore, it is an aspect of one or more exemplary embodiments to provide an X-ray imaging apparatus and an X-ray image generating method by which constituent materials of a target object are separated and mapped to different colors in order to provide one image which is characterized by an improved distinction between tissues.

Additional aspects of the exemplary embodiments will be set forth in part in the description which follows and, in part, will be obvious from the description, or may be learned by practice of the exemplary embodiments.

In accordance with one aspect of one or more exemplary embodiments, an X-ray imaging apparatus includes an X-ray generator which is configured to generate X-rays and to irradiate the X-rays toward a target object, an X-ray detector which is configured to acquire X-ray data which corresponds to a plurality of energy bands by detecting X-rays which have passed through the target object, and a controller which is configured to: acquire a plurality of material images in which a plurality of materials which constitute the target object are respectively displayed and brightness information from the X-ray data, generate a single image by mapping different color channels to each of the acquired plurality of material images and combining the plurality of material images into the single image, and apply the brightness information to the generated single image.

The controller may include an image separation unit which is configured to separate the plurality of material images from the acquired original images based on the plurality of energy bands by using different X-ray attenuation characteristics of the plurality of materials.

The controller may further include a color mapping unit which is configured to map the different color channels to each of the plurality of separated material images.

The X-ray imaging apparatus may further include a display unit which is configured the single image generated by the controller, and a channel conversion unit which is configured to convert color channels of the single image into color channels which are used by the display unit, if the color channels mapped by the color mapping unit and the color channels used by the display unit are different.

In accordance with another aspect of one or more exemplary embodiments, an X-ray image generating method includes irradiating X-rays toward a target object and detecting X-rays which have passed through the target object, acquiring a plurality of material images in which a plurality of materials which constitute the target object are respectively displayed and brightness information from the detected X-rays, mapping different color channels to each of the acquired plurality of material images, and generating a single image by combining the plurality of material images to which the color channels are mapped and applying the acquired brightness information to a result of the combining.

The generating of the single image may include mapping the acquired brightness information to a brightness channel and combining the color channels to which the acquired plurality of material images are mapped and the brightness channel to which the brightness information is mapped.

Further, the generating of the single image may include combining a brightness image which includes the acquired brightness information and the plurality of material images which are mapped to the different color channels.

In accordance with a further aspect of one or more exemplary embodiments, an X-ray imaging apparatus includes an X-ray generator which is configured to irradiate X-rays toward a target object, an X-ray detector which is configured to acquire X-ray data which corresponds to a plurality of energy bands from X-rays which have passed through the target object, and a controller which is configured to generate an X-ray image in which different colors are mapped to respective materials which constitute the target object by using the X-ray data.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1A:
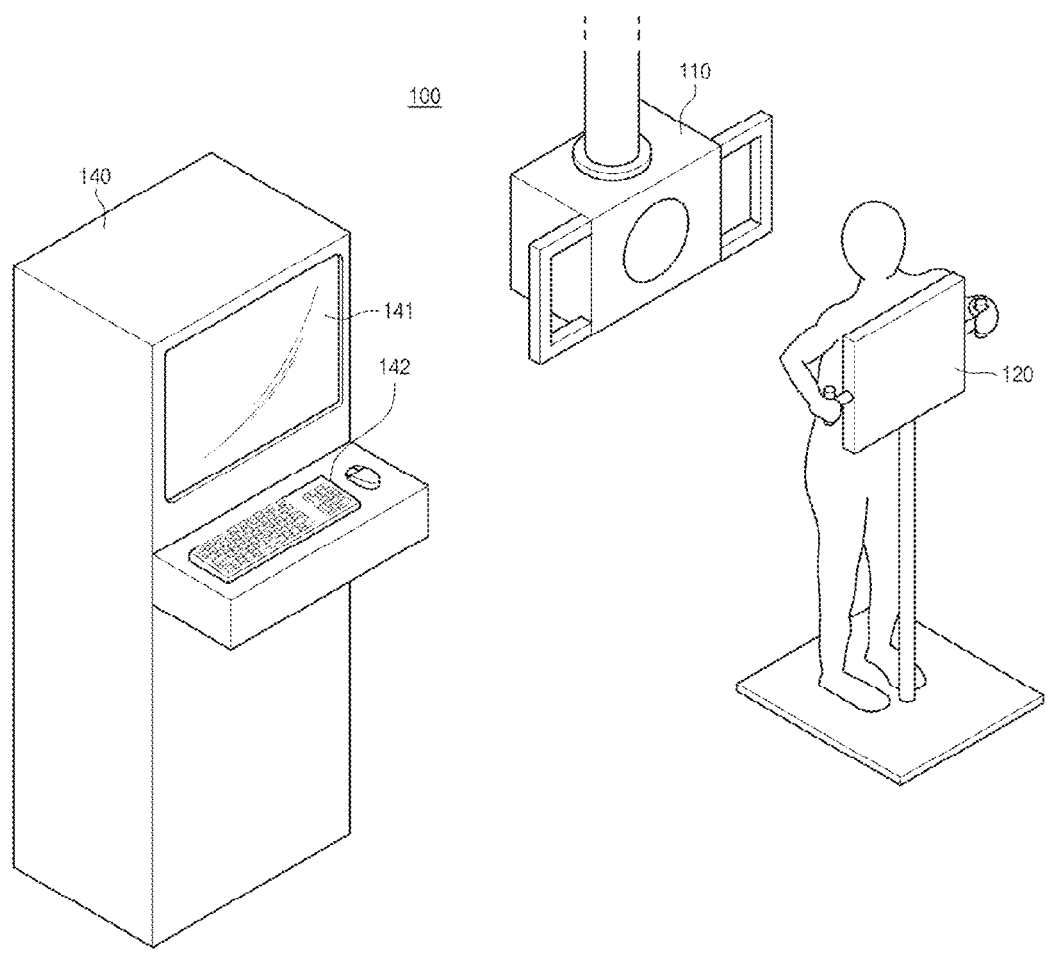
FIG. 1A is a view which illustrates an overall external appearance of an X-ray imaging apparatus which is configured to photograph the chest of a subject patient.

Reference will now be made in detail to exemplary embodiments, examples of which are illustrated in the accompanying drawings, wherein like reference numerals refer to like elements throughout.

An X-ray imaging apparatus may photograph various target objects, and may have different structures based on objects to be photographed. An X-ray imaging apparatus disclosed hereinafter is not limited in target objects thereof, but in order to clearly support the exemplary embodiments, the overall configurations of an X-ray imaging apparatus which is configured to photograph the chest of a subject patient and an X-ray imaging apparatus which is configured to photograph the breast of a subject patient will be described with reference to FIGS. 1A and 1B.

Figure 1B:
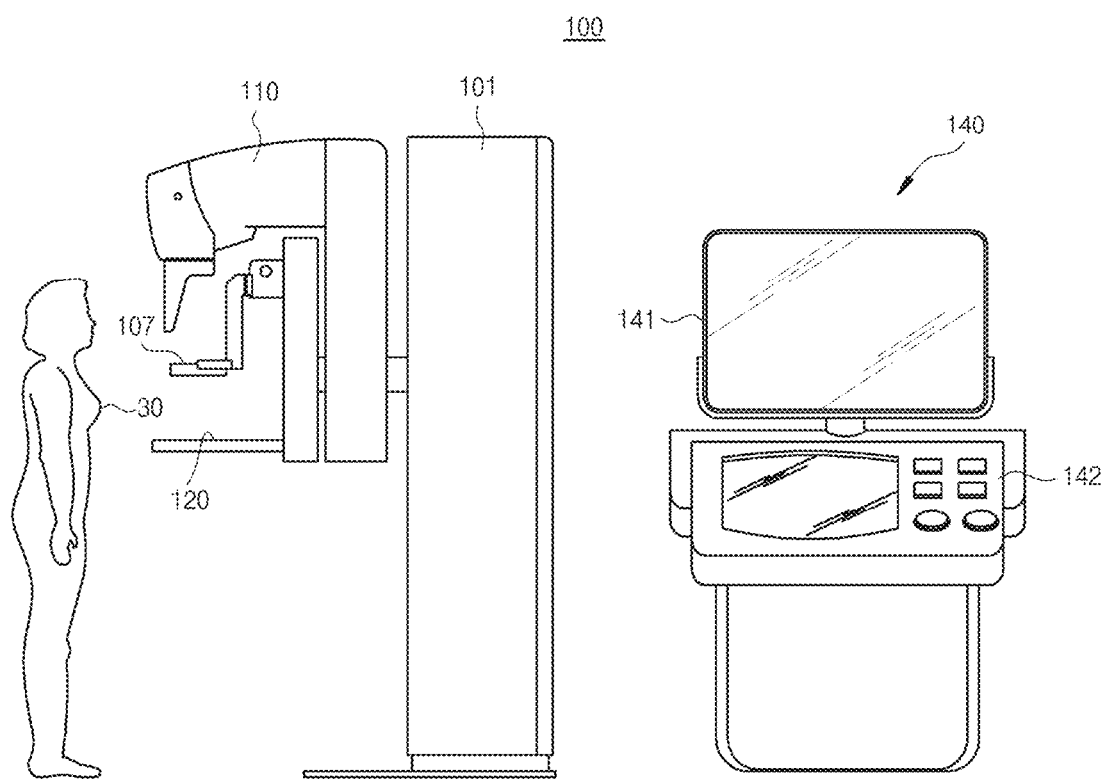
FIG. 1B is a view which illustrates an overall external appearance of an X-ray imaging apparatus which is configured to photograph the breast of a subject patient.

FIG. 1A is a view which illustrates an overall external appearance of the X-ray imaging apparatus which is configured to photograph the chest of a subject patient, and FIG. 1B is a view which illustrates an overall external appearance of the X-ray imaging apparatus which is configured to photograph the breast of a subject patient.

Although FIG. 1A illustrates the X-ray imaging apparatus as photographing the chest, the X-ray imaging apparatus of FIG. 1A may photograph other target objects than the chest, such as, for example, arms or legs or any other body part of a subject patient.

However, in case of the breast, which consists of only soft tissues, in order to obtain a clearer and more correct image, compression in the vertical direction may be required, and thus the X-ray imaging apparatus which is configured to photograph the breast has a different structure from the X-ray imaging apparatus of FIG. 1A.

With reference to FIGS. 1A and 1B, the X-ray imaging apparatus 100 includes an X-ray generator 110 which generates X-rays and irradiates the X-rays toward a target object, an X-ray detector 120 which detects X-rays which have passed through the target object, and a host device (or a workstation) 140 which generates and displays an X-ray image which relates to the target object by using the detected X-rays.

Because the X-rays irradiated from the X-ray generator 110 penetrate the target object and are detected by the X-ray detector 120, the target object is located between the X-ray generator 110 and the X-ray detector 120 during X-ray radiography, as shown in FIGS. 1A and 1B.

Further, in the case of the breast 30, compression in the vertical direction may be required, as described above. Therefore, the X-ray imaging apparatus 100 which is configured to photograph the breast 30 further includes a pressing paddle 107 which is arranged between the X-ray generator 110 and the X-ray detector 120, and the X-ray generator 110, the X-ray detector 120 and the pressing paddle 107 are supported by a housing 101, as shown in FIG. 1B.

The host device 140 includes a display unit 141 which displays the generated X-ray image, and an input unit 142 which receives various instructions regarding operation of the X-ray imaging apparatus 100 which may be input by a user. Further, the host device 140 may execute a process for generating the X-ray image by using X-ray data which is received from the X-ray detector 120, if the host device 140 is provided with a controller which will be described later. The display unit 141 may include, for example, a monitor, a screen, and/or any other suitable type of display. The input unit 142 may include, for example, a keyboard, a mouse, a joystick, and/or any other suitable device which is suitable for providing user input to the host device 140.

Hereinafter, the detailed configuration and operation of an X-ray imaging apparatus in accordance with an exemplary embodiment will be described.

Figure 2:
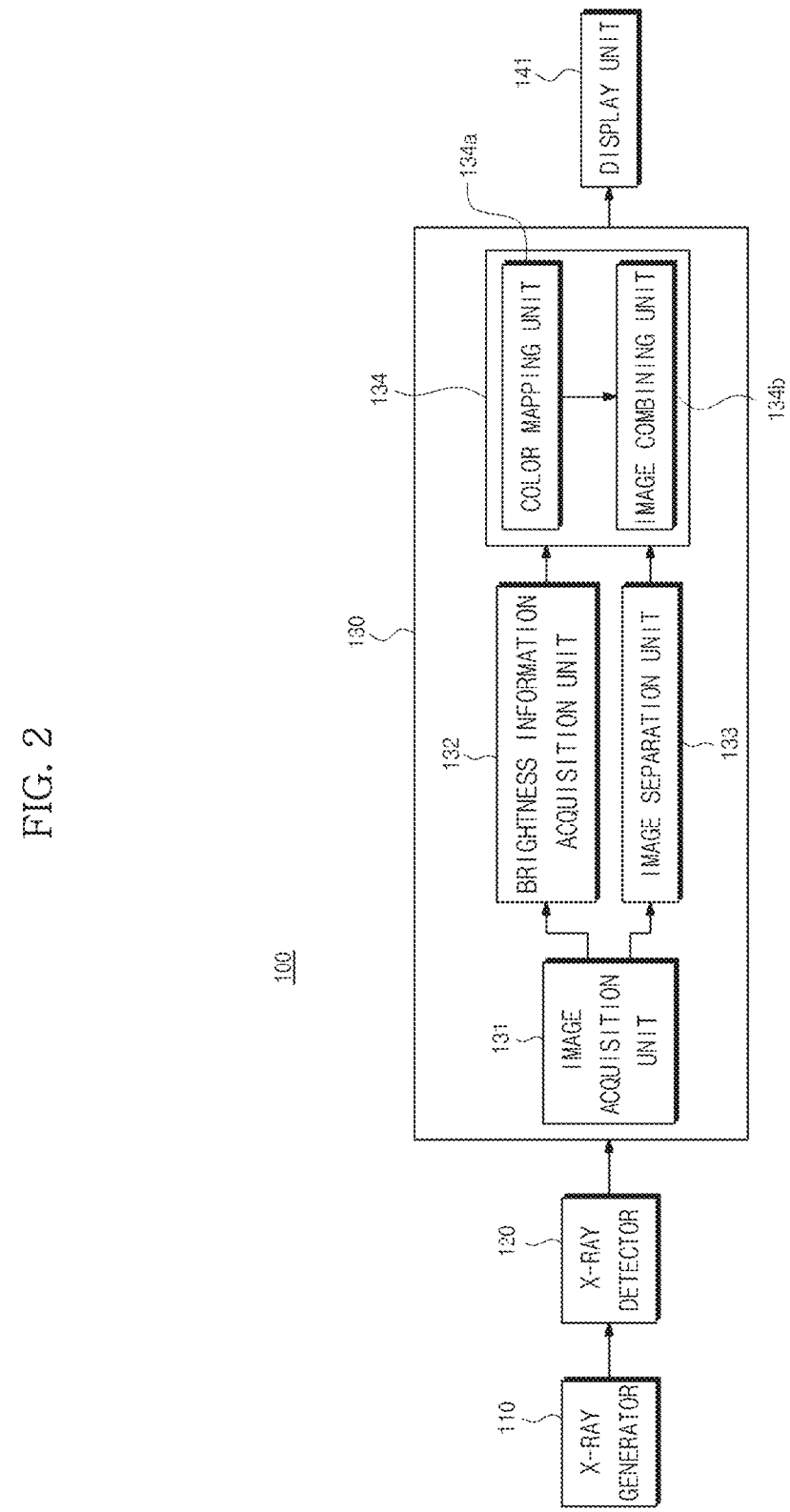
FIG. 2 is a control block diagram of an X-ray imaging apparatus, in accordance with an exemplary embodiment.

FIG. 2 is a control block diagram of an X-ray imaging apparatus in accordance with an exemplary embodiment.

With reference to FIG. 2, the X-ray imaging apparatus 100 in accordance with the exemplary embodiment includes, in addition to the above-described X-ray generator 110 and X-ray detector 120, a controller 130 which is configured to generate an X-ray image in which different colors are mapped based on respective materials of a target object by using X-ray data which is received from the X-ray detector 120, and a display unit 141 which displays the generated X-ray image.

Although the controller 130 may be provided on the host device 140 of the X-ray imaging apparatus, as described above, exemplary embodiments are not limited thereto. In particular, the position of the controller 130 is not limited, provided that the controller 130 may execute functions which will be described below.

As described above, the X-ray generator 110 generates X-rays and irradiates the X-rays toward a target object. The X-ray generator 110 generates the X-rays by using power which is supplied from a power supply (not shown). The energy of the X-rays may be controlled by a tube voltage, and the intensity or dose of the X-rays may be controlled by a tube current and by an X-ray exposure time.

Although the X-ray generator 110 may irradiate monochromatic X-rays or polychromatic X-rays, this exemplary embodiment illustrates the X-ray generator 110 as irradiating polychromatic X-rays which have a designated energy band, and the designated energy band of the irradiated X-rays is defined by the upper and lower limits.

The upper limit of the energy band, i.e., the maximum energy of the irradiated X-rays, may be adjusted by adjusting the intensity of tube voltage, and the lower limit of the energy band, i.e., the minimum energy of the irradiated X-rays, may be adjusted by using a filter which is provided at the inside or the outside of the X-ray generator 110. When X-rays of the lower energy band are filtered by the filter, a mean energy level of the irradiated X-rays may be raised.

The X-ray imaging apparatus 100 may include an auto exposure controller (AEC) which is configured to adjust parameters for X-ray irradiation, such as, for example, a parameter which relates to at least one of a tube voltage, a tube current, a target material of an anode, an exposure time, and a filter type. This optimizes irradiation conditions of X-rays based on a target object which is actually to be photographed, and the AEC may set parameters which are optimized based on characteristics of the target object by analyzing a pre-shot image of the target object.

The X-ray detector 120 detects X-rays which have passed through the target object, and obtains X-ray data by converting the detected X-rays into an electrical signal. For example, the X-ray detector 120 may include a light receiving element which generates electric charges when photons of X-rays reach the light receiving element, and a readout circuit which reads and processes an electrical signal from the generated electric charges. As the light receiving element, for example, materials of at least one of a-S, a-Se, CdZnTe, HgI2, and PbI2 may be used.

X-ray detectors may be divided into a charge integration type in which electric charges are stored for a designated time and then a signal is acquired from the electric charges, and a photon counting type in which a signal is counted whenever the signal is generated by a signal X-ray photon, based on corresponding electrical signal acquisition methods. Any of the two types may be applied to the X-ray detector 120 in accordance with an exemplary embodiment.

The controller 130 may acquire material images in which materials which constitute the target object are respectively displayed, as described above. For this purpose, the controller 130 may acquire X-ray images based on a plurality of energy bands from the X-ray detector 120. Hereinafter, the operation of the X-ray imaging apparatus 100 in order to acquire X-ray images based on a plurality of energy bands will be described in detail.

Figure 3:
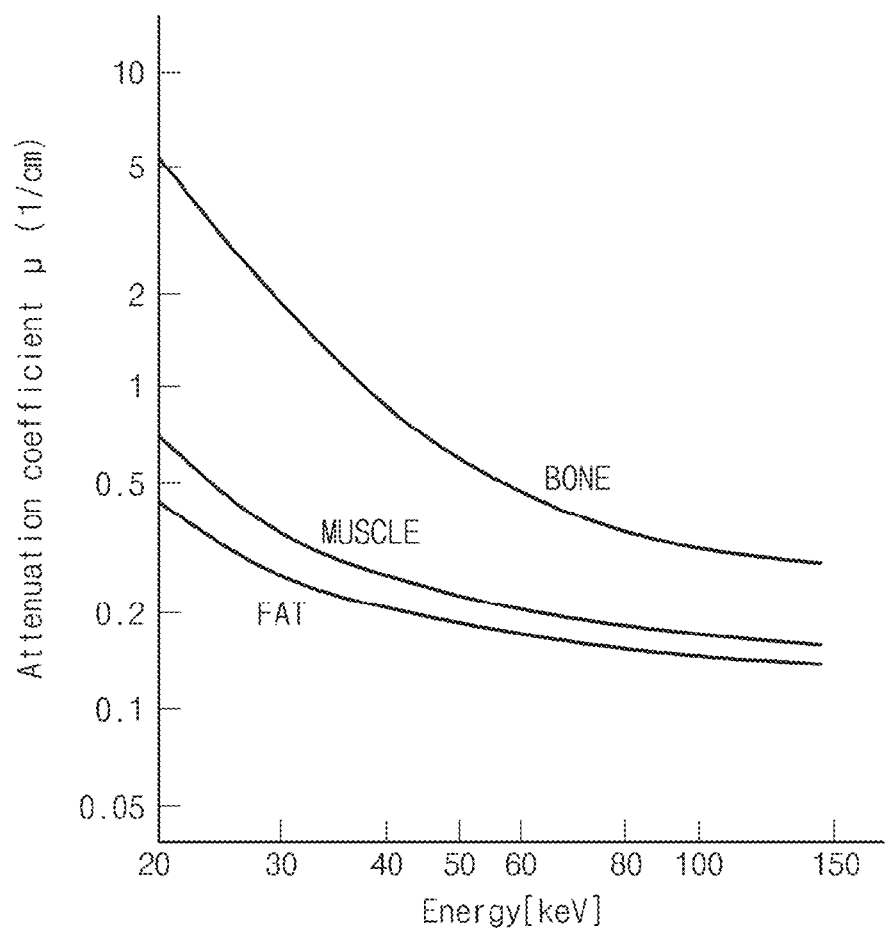
FIG. 3 is a graph which represents X-ray attenuation coefficients based on constituent materials of a target object.
Figure 4A:
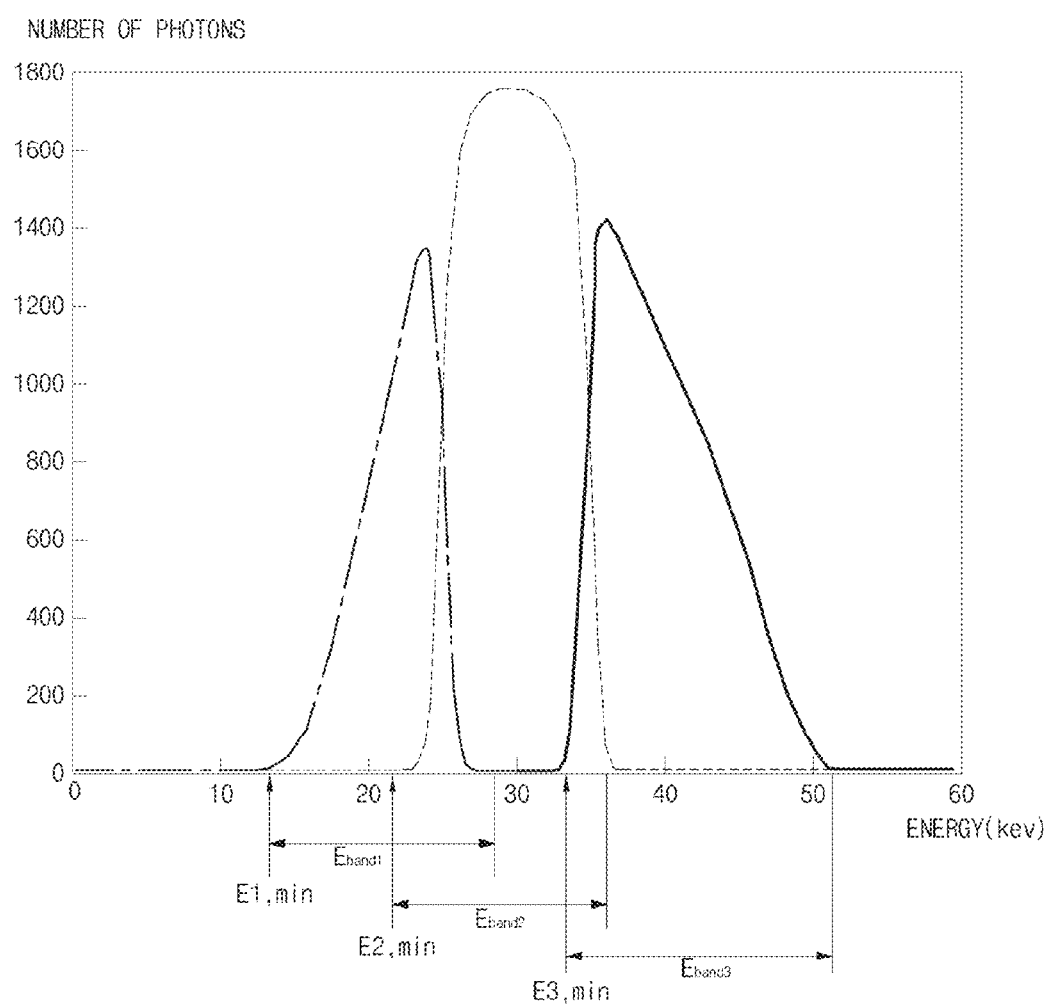
FIG. 4A is a graph which represents an X-ray spectrum which is separated based on energy bands.
Figure 4B:
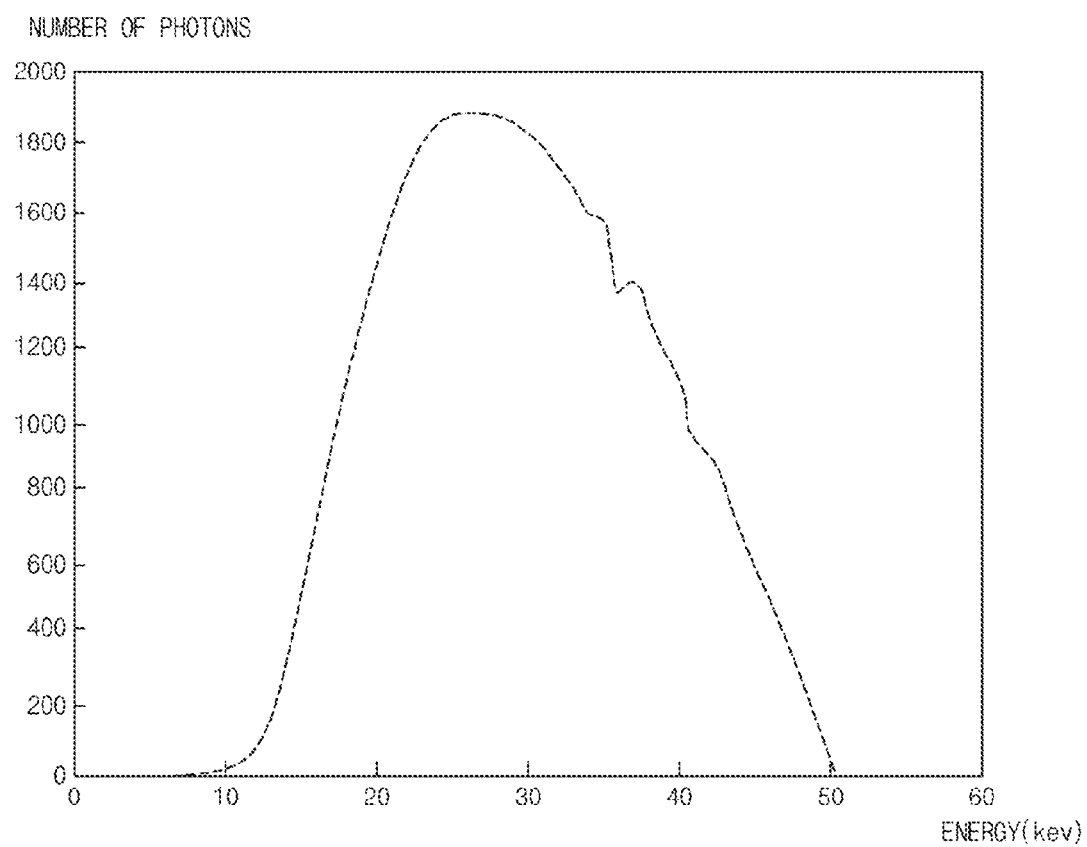
FIG. 4B is a graph which represents an example of an X-ray spectrum which has been irradiated from an X-ray generator.

FIG. 3 is a graph which represents X-ray attenuation coefficients based on respective constituent materials of a target object, FIG. 4A is a graph which represents an X-ray spectrum which is separated based on the plurality of energy bands, and FIG. 4B is a graph which represents an example of an X-ray spectrum which is irradiated from the X-ray generator. Although, for convenience, the vertical axis of the graph of FIG. 4A or 4B represents the number of photons, the vertical axis may represent the intensity of X-rays.

X-rays exhibit a transmission factor or an attenuation factor which varies based on materials which are used for transmitting the X-rays, and an X-ray image expresses the interior of a target object by using such a phenomenon. An attenuation coefficient numerically represents the attenuation factor of X-rays, and may be expressed by Equation 1 below.

$$I=I_0 * \exp(-\mu t)$$ [Equation 1]

In particular, I indicates an intensity of X-rays which have passed through the target object, $I_0$ indicates an intensity of X-rays which are incident upon the target object, $-\mu$ is an attenuation coefficient, and t indicates a thickness of the target object.

With reference to FIG. 3, as the energy of X-rays increases, the attenuation coefficient of a constituent material decreases, and therefore, when the energy of X-rays is high, the X-rays easily penetrate the target object. Further, an attenuation curve which corresponds to bones is located above an attenuation curve which corresponds to muscles and an attenuation curve which corresponds to fat, and therefore, the transmission factor of X-rays with respect to soft tissues, such as muscles or fat, is higher than the transmission factor of X-rays with respect to bones.

From the graph of FIG. 3, it may be understood that a difference of the attenuation coefficients between materials varies based on the corresponding intensities of energy. In detail, as the energy of X-rays increases, a difference of the attenuation coefficients between the materials decreases. Therefore, when X-ray images of different energy bands are acquired and attenuation characteristics of materials at the respective energy bands are used, separated images of the respective materials may be acquired from the corresponding X-ray images of the different energy bands.

For example, in order to acquire images of three materials, X-ray images which correspond to different energy bands $E_{band1}$, $E_{band2}$ and $E_{band3}$ are acquired, as shown in FIG. 4A.

As methods for acquiring X-ray images based on different energy bands, there are a method by which the X-ray generator 110 irradiates X-rays plural times while varying an energy band, and a method by which the X-ray generator 110 irradiates wide band X-rays which include a plurality of energy bands one time and the X-ray detector 120 detects the wide band X-rays and separates the wide band X-rays based on the plurality of energy bands.

If the former method is executed by using the X-ray imaging apparatus 100, the X-ray generator 110 irradiates X-rays of an energy band $E_{band1}$, and the X-ray detector 120 detects the X-rays and thus acquires an X-ray image which corresponds to the energy band $E_{band1}$. In case of energy bands $E_{band2}$ and $E_{band3}$, X-ray images corresponding thereto are acquired in the same manner.

If the latter method is executed by using the X-ray imaging apparatus 100, the X-ray generator 110 irradiates wide band X-rays which include three energy bands one time, as shown in FIG. 4B, and the X-ray detector 120 detects the wide band X-rays and separates the wide band X-rays based on the respective energy bands.

The energy of X-rays irradiated from the X-ray generator 110 varies based on respective target objects. For example, if the target object is the breast, the X-ray generator 110 may generate and irradiate X-rays of an energy, the lower limit of which is 10 keV and the upper limit of which is 50 keV, as shown in FIG. 4B. For this purpose, the X-ray generator 110 may generate X-rays by using a tubular voltage of 50 kvp, filter a low energy band (approximately with the range of 0-10 keV) of the X-rays, and then irradiate the filtered X-rays. In particular, the dose (i.e., the number of photons) of the X-rays, which may be expressed as the y-axis, may be controlled by controlling one or both of a tubular current and an X-ray exposure time.

Figure 5:
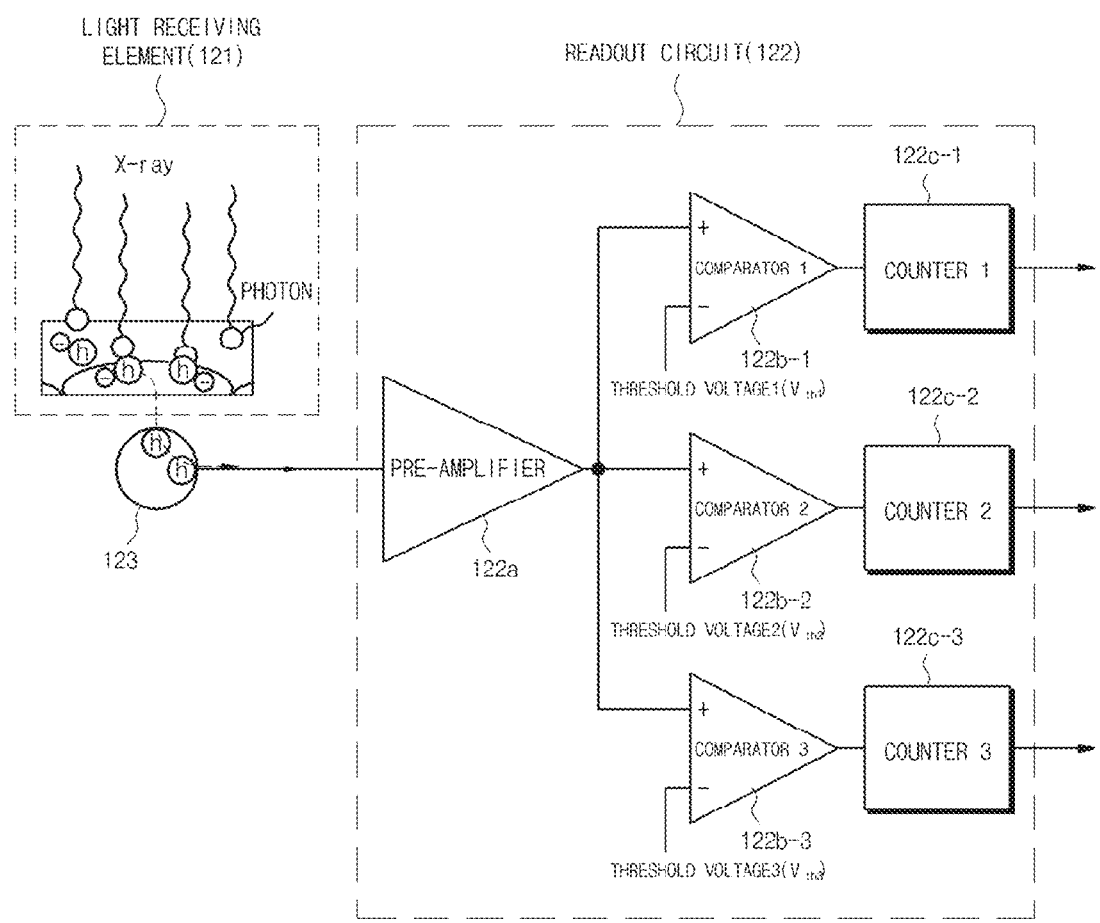
FIG. 5 is a view which illustrates a single pixel structure of a photon counting type X-ray detector.

In order to separate the detected X-rays based on the energy bands, the X-ray detector 120 is implemented in the photon counting type. FIG. 5 is a view which illustrates a single pixel structure of the photon counting type X-ray detector 120.

With reference to FIG. 5, when photons of X-rays are incident upon the light receiving element 121, electrons in a valence band receive energy of the photons, pass a band gap energy difference, and are excited to a conduction band. Thereby, electron-hole pairs are generated in a depletion region.

When a metal electron is formed on the light receiving element 121 and a reverse bias is applied to the light receiving element 121, electrons among the electron-hole pairs generated in the depletion region are moved to an n-type region, and holes are moved to a p-type region. Then, the holes which have moved to the p-type region are input to the readout circuit 122 through bump bonding 123 so that an electrical signal generated by the photons may be read. However, based on the structure of the light receiving element 121 and the applied voltage, the electrons may be input to the readout circuit 122 so as to generate an electrical signal.

The readout circuit 122 may be formed in a 2D pixel array structure, and reads electrical signals based on respective pixels. When electric charges are input to the readout circuit 122 from the light receiving element 121 through bump bonding 123, a pre-amplifier 122a of the readout circuit 122 accumulates an input charge which is generated from one photon and outputs a voltage signal which corresponds thereto.

The voltage signal which is output from the pre-amplifier 122a is input to a comparator 122b, the comparator 122b compares the received input voltage signal with a threshold voltage which is controllable from the outside and outputs a pulse signal of "1" or "0" based on a result of the comparison, and a counter 122c counts the number of pulse signals of "1" and outputs X-ray data in a digital form. An X-ray image of the target object may be acquired by combining X-ray data based on pixels.

In particular, the threshold voltage corresponds to a threshold energy E, and, if the number of photons which have an energy which exceeds the threshold energy E is counted, the threshold voltage which corresponds to the threshold energy E is input to the comparator 122b. The reason for correspondence between the threshold energy and the threshold voltage is that the intensity of the electrical signal (i.e., the voltage) generated from the light receiving element varies based on the energy of the photons. Therefore, a threshold voltage which corresponds to a desired threshold energy may be calculated by using a relation formula between energy of photons and generated voltage, and in the exemplary embodiment which will be described in detail below, an input of a threshold energy to the X-ray detector 120 may have the same meaning as an input of a threshold voltage which corresponds to the threshold energy.

In order to separate the detected X-rays based on the plurality of energy bands, a plurality of comparators may be provided. Although the embodiment of FIG. 5 illustrates three comparators, the exemplary embodiments are not limited thereto, and the number of comparators may be set, for example, based on a number of energy bands into which the X-rays are separated.

When electrons or holes which are generated by a single photon are input to the pre-amplifier 122a through bump bonding, and the pre-amplifier 122a outputs a voltage signal, such a voltage signal is input to the three comparators 122b-1, 122b-2 and 122b-3. Then, when the respective threshold voltages 1 $V_{th1}$, 2 $V_{th2}$, and 3 $V_{th3}$ are input to the respective comparators 122b-a, 122b-2 and 122b-3, the comparator 1 122b-1 compares the input voltage with the threshold voltage 1 $V_{th1}$, and the counter 1 122c-1 counts the number of photons which generate a voltage which is greater than the threshold voltage 1 $V_{th1}$. In the same manner, the counter 2 122c-2 counts the number of photons which generate a voltage which is greater than the threshold voltage 2 $V_{th2}$, and the counter 3 122c-3 counts the number of photons which generate a voltage which is greater than the threshold voltage 3 $V_{th3}$.

The numbers of photons based on energy bands, as counted by the X-ray detector 120, i.e., X-ray data, are input to the controller 130 in a digital form. The controller 130 acquires separated images of materials of the target object by using the X-ray data, maps different color channels to the respective separated images, and then combines the separated images into one single image.

The materials which correspond to the separated images are not limited, and may be any materials having different X-ray absorption coefficients. For example, the separated materials may be bones and soft tissues, lesion tissues and non-lesion tissues, or calcifying tissues and non-calcifying tissues. The calcifying tissues may include calcifying nodules, and the non-calcifying tissues may include non-calcifying nodules.

Calcification is a process by which calcium salts build up in tissues, and bones and calcifying tissues may have similar X-ray absorption characteristics. Therefore, a first material which includes at least one of bones and calcifying tissues and a second material which includes at least one of soft tissues and non-calcifying tissues may be separated.

Further, if the target object is the breast, at least one material selected from the group consisting of fat tissues, parenchymal tissues, calcifying tissues and lesion tissues may be separated.

With reference to FIG. 2, the controller 130 includes an image acquisition unit 131 which acquires X-ray images based on the respective plurality of energy bands from the X-ray data which is received from the X-ray detector 120, a brightness information acquisition unit 132 which acquires brightness information from the acquired images, an image separation unit 133 which separates material images from the acquired images, and an image generation unit 134 which maps different color channels to the respective separated material images and generates a final image by combining these images and applying the brightness information which is acquired by the brightness information acquisition unit 132 to a result of the combining. Each of the image acquisition unit 131, the brightness information acquisition unit 130, the image separation unit 133, and the image generation unit 134 may be embodied, for example, as a hardware component, such as a microprocessor chip or as integrated circuitry, or as a software module.

The image acquisition unit 131 receives the X-ray data based on the respective plurality of energy bands from the X-ray detector 120, and acquires X-ray images which correspond to the respective energy bands. The X-ray images acquired by the image acquisition unit 131 may include, for example, the X-ray data themselves as received from the X-ray detector 120, i.e., raw images, or reverse images which are formed by applying a correction to the received X-ray data.

Figure 6A:
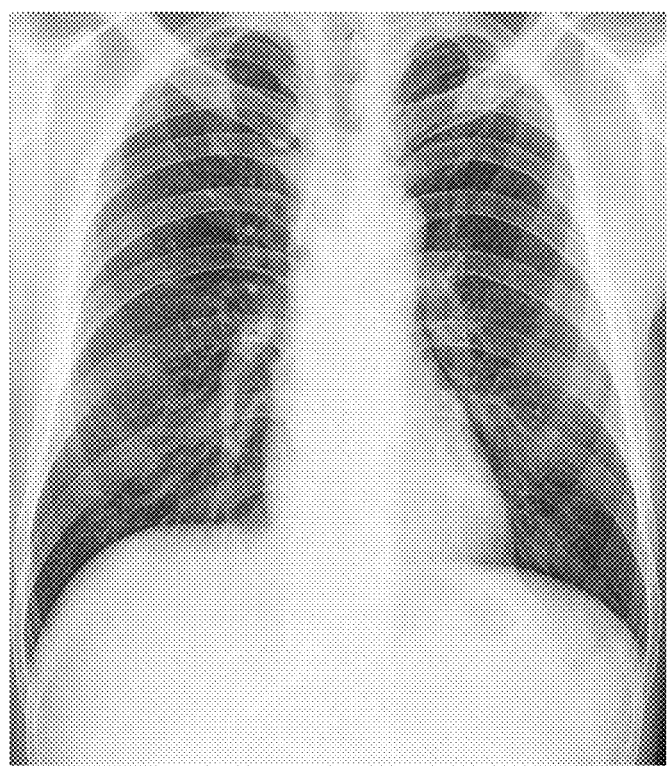
FIG. 6A is a chest image which corresponds to X-rays of a low energy band.
Figure 6B:
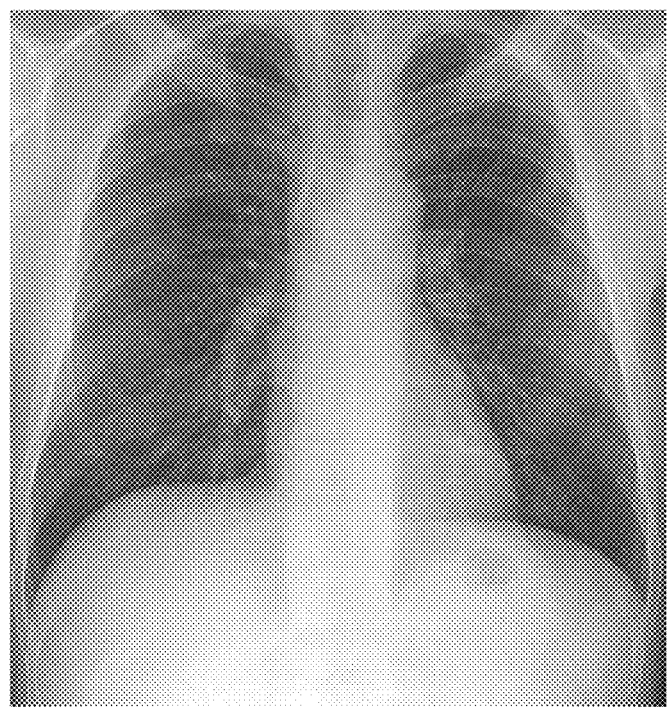
FIG. 6B is a chest image which corresponds to X-rays of a high energy band.

FIG. 6A illustrates a chest X-ray image which corresponds to a relatively low energy band, and FIG. 6B illustrates a chest X-ray image which corresponds to a relatively high energy band. In the exemplary embodiment which will be described in detail below, images which correspond to respective energy bands in which a separation of materials is not shown are referred to as original images.

As one example, if two kinds of materials are desired to be separated from chest images, the two kinds of materials to be separated must have different X-ray attenuation characteristics, and chest X-ray images which correspond to two different energy bands must be acquired. For example, bones and soft tissues within a chest image have different X-ray attenuation characteristics from one another, and thus a bone image and a soft tissue image may be separated from chest X-ray images which correspond to two different energy bands.

In order to acquire chest X-ray images which correspond to two different energy bands, the X-ray generator 110 may respectively irradiate X-rays of a high energy band and X-rays of a low energy band; or the X-ray generator 110 may irradiate wide band X-rays which include the two energy bands, and the X-ray detector 120 may separate the detected X-rays into the high energy band and the lower energy band.

In particular, the "high energy band" and the "low energy band" are relative terms, and may vary based on target objects. For example, if the target object is the chest, an energy band which has a maximum energy of 140 keV may become a high energy band and an energy band which has a maximum energy of 70 keV may become a low energy band, and if the target object is the breast, an energy band which has a maximum energy of 30 keV may become a low energy band and an energy band which has a maximum energy of 50 keV may become a high energy band.

With reference to FIGS. 6A and 6B, it is understood that a brightness difference between bones and soft tissues is detectable in the X-ray image of the low energy band and the X-ray image of the high energy band. The reason for this is that an attenuation characteristic difference between constituent materials varies based on energy bands, and the image separation unit 133 which will be described below may separate material images from the two original images by using this phenomenon.

The original images which are acquired by the image acquisition unit 131 are input to the brightness information acquisition unit 132 and the image separation unit 133.

The brightness information acquisition unit 132 acquires brightness information, which will be applied to the final image to be generated by the image generation unit 134, from the original images. In more detail, the brightness information acquisition unit 132 may select one of the original images which is acquired by the image acquisition unit 131 and directly employ brightness information which is included in the selected original image, may generate a mean image with respect to the original images and employ brightness information of the mean image, or may employ brightness information which is included in a weighted sum image which is generated by computing a weighted sum of the original images. Because the original images, the mean image and the weighted sum image are all black and white images and represent brightness information, brightness information may refer to each image itself.

The image separation unit 133 separates material images from the original images which are acquired by the image acquisition unit 131.

Figure 7A:
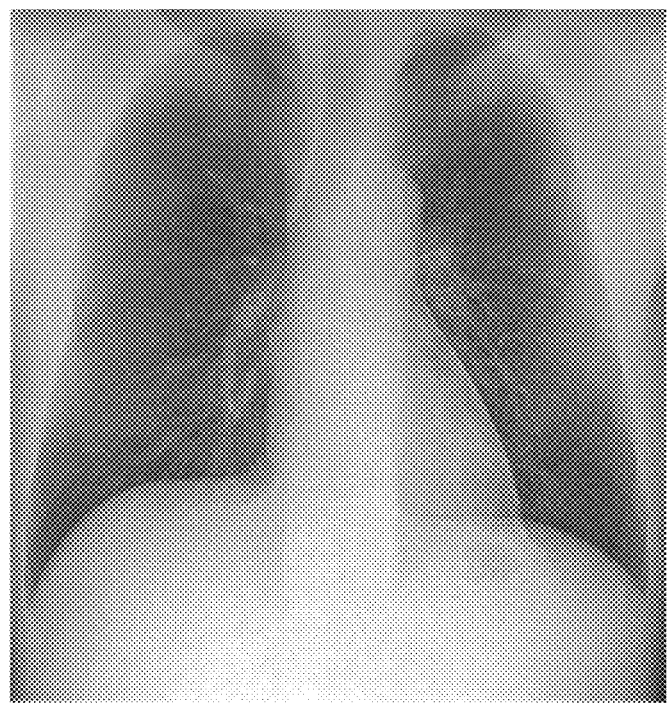
FIG. 7A is a soft tissue image which has been separated from a chest X-ray image.
Figure 7B:
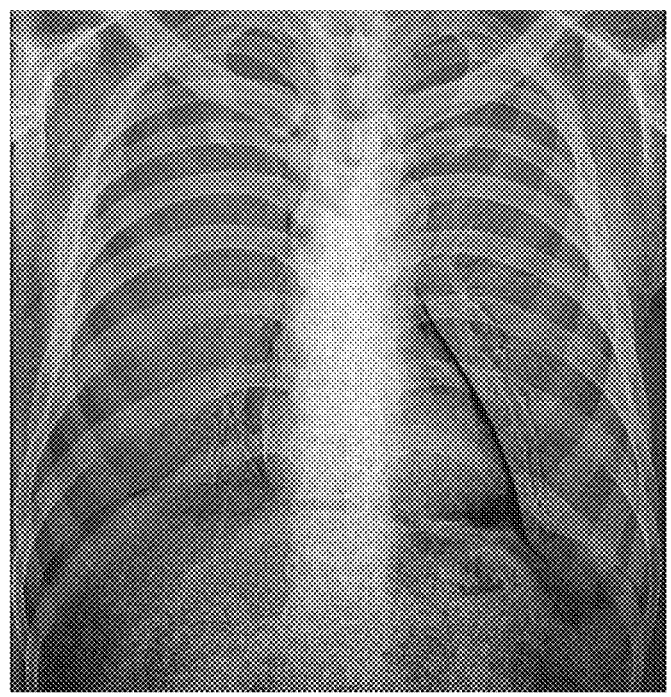
FIG. 7B is a bone image which has been separated from a chest X-ray image.

FIG. 7A is a soft tissue image which has been separated from a chest image, and FIG. 7B is a bone image which has been separated from a chest image.

As one example, if two kinds of materials are desired to be separated from the chest image, the image acquisition unit 131 may acquire two original images which correspond to two respective energy bands, and the image separation unit 133 may separate two material images from the original images by executing two calculations in which at least one of the two original images is multiplied by a weight and then subtraction is executed. This technique is referred to as Dual-Energy X-ray Absorptiometry.

As one example, if the materials desired to be separated from the chest image are bones and soft tissues, a soft tissue image, as shown in FIG. 7A, may be acquired by multiplying the original image which corresponds to the low energy band (hereinafter, referred to as a low energy image) by a designated weight and then subtracting a resultant value from the original image which corresponds to the high energy band (hereinafter, referred to as a high energy image). In this manner, an image in which soft tissues are clearly seen without bones may be acquired.

Conversely, a bone image, as shown in FIG. 7B, may be acquired by multiplying the high energy image by a designated weight and then subtracting a resultant value from the low energy image. In this manner, an image in which bones are clearly seen without soft tissues may be acquired.

Otherwise, a soft tissue image or a bone image may be acquired by respectively multiplying each of the low energy image and the high energy image by proper respective weights and then executing a respective subtraction to each.

Further, if the materials desired to be separated are lesion tissues and non-lesion tissues, or calcifying tissues and non-calcifying tissues, the above-described method may be applied. However, based on which region the target object corresponds to, a lesion tissue may be included in a calcifying tissue, or may be included in a non-calcifying tissue.

As another example, if the target object is the breast, which includes soft tissues, and the materials desired to be separated from breast images are glandular tissues (referred to as parenchymal tissues) and adipose tissues, a glandular tissue image and an adipose tissue image may be acquired by respectively multiplying a low energy image and a high energy image by proper weights and then executing a respective subtraction to each.

As another example, if three or more kinds of materials are desired to be separated from an image, the image acquisition unit 131 may acquire three or more original images which correspond to three or more respective energy bands, and the image separation unit 133 may separate three or more material images from the original images by multiplying the respective original images by proper weights and executing a respective subtraction to each. In more detail, if the target object is the breast, images of three or more kinds of materials which are selected from the group consisting of adipose tissues, parenchymal tissues, calcifying tissues and lesion tissues may be separated from the original images.

As described above, the X-ray imaging apparatus 100 is not limited in kinds of materials to be separated or the number of the materials to be separated, and may acquire original images which correspond in number to the number of the materials to be separated, and separate respective material images from the original images by using attenuation characteristics based on the materials.

Further, the method of separating material images from original images by multiplying the original images by weights and then executing subtraction is only one exemplary method used by the image separation unit 133, and other methods than such a method may be used in order to perform a separation of material images.

With reference to FIG. 2, the image generation unit 134 includes a color mapping unit 134a which maps different color channels to the respective material images separated by the image separation unit 133 and an image combining unit 134b which combines the material images to which the different color channels are mapped and applies the brightness information acquired by the brightness information acquisition unit 132 to a result of the combining.

The color mapping unit 134a maps different color channels to the respective material images separated by the image separation unit 133. For example, if the image separation unit 133 separates two kinds of materials from original images, a first color channel is mapped to the first separated material image and a second color channel is mapped to the second separated material image, and if the image separation unit 133 separates three kinds of materials from original images, a first color channel is mapped to the first separated material image, a second color channel is mapped to the second separated material image, and a third color channel is mapped to the third separated material image.

Further, the image combining unit 134b combines the plurality of material images to which the different color channels are mapped, and applies the brightness information acquired by the brightness information acquisition unit 132 thereto, thus generating one single image. In particular, the image combining unit 134b generates one image by combining the color channels to which the respective material images are mapped and a brightness channel to which brightness information or a brightness image which is acquired by the brightness information acquisition unit 132 is mapped.

Hereinafter, the operation of the color mapping unit 134a and the image combining unit 134b will be described in detail.

The color mapping unit 134a may map color channels using any one or more of various color spaces. For example, the color mapping unit 134a may use at least one color space from among a YUV color space, an HSI color space, an HSV color space and an HSL color space in which color information and brightness information are separated, and a CMY color space, a CMYK color space and an RGB color space in which color information includes brightness information.

In more detail, the case in which the YUV color space is used will be exemplarily described. The YUV color space expresses an image by using brightness information (Y) and color information (U, V). The color information (U,V) may be representatively indicated by Cb and Cr. In particular, Cb is a color difference value which relates to a blue, and Cr is a color difference value which relates to a red.

If the image separation unit 133 separates two material images from original images, the color mapping unit 134a may map a Cb channel to the first separated material image and map a Cr channel to the second separated material image.

When the image combining unit 134b maps a Y channel which represents brightness information to the brightness image acquired by the brightness information acquisition unit 132 and combines the brightness image with the first separated material image which is mapped to the Cb channel and the second separated material image which is mapped to the Cr channel, the first material and the second material are finally mapped to different colors, and thus, a distinction between the materials may be improved, and a brightness of the original images is applied, and thus one image in which artifacts are reduced may be generated.

Next, the HSI color space will be exemplarily described. The HSI color space expresses an image with respect to Hue, Saturation and Intensity. Therefore, the color mapping unit 134a maps different colors to the respective material images, and the image combining unit 134b combines the material images to which the different colors are mapped and applies the brightness information acquired by the brightness information acquisition unit 132 thereto. In particular, the color channels to which the material images are mapped and the brightness channel to which the brightness information is mapped are combined.

When the colors are mapped, a saturation may have a fixed value, or different saturation values may be mapped to the material images.

Although the above-described exemplary embodiment employs the color spaces in which brightness information and color information are separated, exemplary embodiments may employ color spaces in which color information includes brightness information.

The above-stated CMY color space, CMYK color space and RGB color space are color spaces in which color information includes brightness information. For example, if the RGB color space is applied, the color mapping unit 134a may respectively map a red channel and a blue channel to two separated material images, and the image combining unit 134b may map a brightness image to a green channel which is seen most brightly and combine the green channel with the red channel and the blue channel.

If the CMYK color space is used, respective material images may be mapped to two or three channels from among a cyan (C) channel, a magenta (M) channel, a Y (yellow) channel and a K (black) channel, a brightness image may be mapped to a remaining channel to which the material images are not mapped, and these channels may be combined.

If the material desired to be separated is lesion tissues, different colors may be mapped based on respective progress stages of the lesion tissues, so that a user may recognize the progress stage of the lesion tissues while observing an X-ray image. In more detail, a case in which the RGB color space is used will be exemplarily described. When the image separation unit 133 separates a lesion tissue image from an original image, the color mapping unit 134a maps a red channel to the lesion tissue image. In particular, the color mapping unit 134a may map different values of the red channel to the lesion tissue image, based on respective progress stages of the lesion tissues.

The progress stage of the lesion tissues is estimated by a brightness value of the original images or the material images, and thus the color mapping unit 134a may map different values of the red channel based on brightness values of the lesion tissues. For example, if cancer cells as lesion tissues are generated in soft tissues, the brightness value of the lesion tissues may be increased due to dehydration. Therefore, because, as the brightness value increases, it is estimated that the lesion tissues progress, as the brightness value increases, the progress stage of the lesion tissues may be expressed by mapping a higher red channel value or a lower red channel value.

Further, kinds or ratios of components which constitute the lesion tissues may be varied based on progress stages of the lesion tissues. Therefore, the color mapping unit 134a may map different colors to the lesion tissues based on progress stages of the lesion tissues without consideration of the brightness value of the lesion tissues. In particular, a first color which is mapped to late-stage lesion tissues and a second color which is mapped to early-stage lesion tissues may be different.

Figure 8:
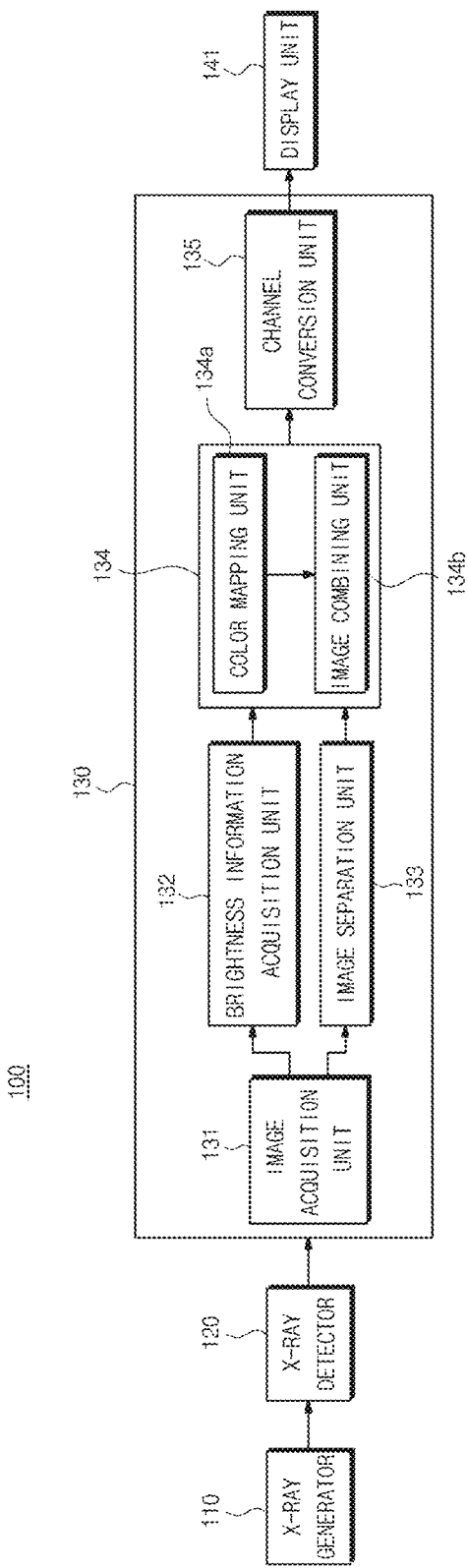
FIG. 8 is a control block diagram of an X-ray imaging apparatus which includes a channel conversion unit, in accordance with another exemplary embodiment.

The above description is only exemplary to represent the progress stage of lesion tissues, and the used color space or the color channel mapped to the lesion tissues are not limited thereto. FIG. 8 is a control block diagram of an X-ray imaging apparatus which includes a channel conversion unit, in accordance with another exemplary embodiment.

With reference to FIG. 8, the X-ray imaging apparatus 100 in accordance with this exemplary embodiment may further include a channel conversion unit 135 which converts color channels of an image which is generated by the image generation unit 134 so as to suit the specifications of the display unit 141, if the color channels of the image which is generated by the image generation unit 134 are different from color channels which are used by the display unit 141.

For example, if the image generation unit 134 generates an image by using an YCbCr color space but the display unit 141 displays an image by using an RGB color space, the channel conversion unit 135 may converts YCbCr color channels into RGB color channels based on Equation 2 below.

$$R = 1.0000Y + 1.402000Cr$$

$$G = 1.0000Y - 0.34414Cb - 0.71414Cr$$

$$B = 1.0000Y + 1.77200Cb \qquad \text{[Equation 2]}$$

However, there are several equations which may be interchangeably used in order to convert the YCbCr color channels into the RGB color channels, in addition to Equation 2, and the channel conversion unit 134 may use any equation from among these equations, including Equation 2.

Because there are conversion equations between other color channels, if a color space used in the image which is generated by the image generation unit 134 and a color space which is used by the display unit 141 are different, the channel conversion unit 135 may execute a color channel conversion by using a corresponding conversion equation between color channels, and then the display unit 141 may display an image. Hereinafter, an X-ray image generating method in accordance with an exemplary embodiment will be described.

Figure 9:
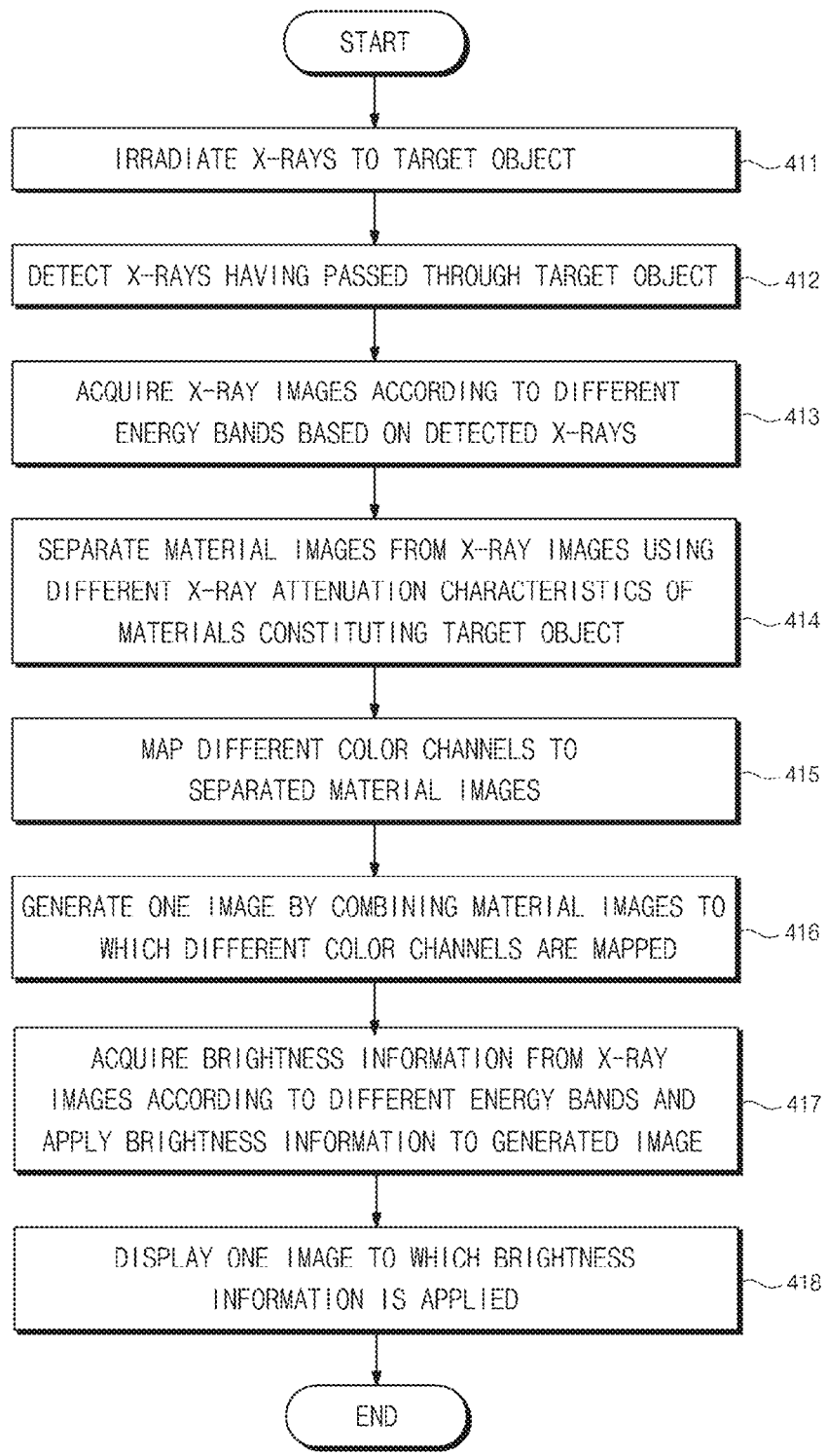
FIG. 9 is a flowchart which illustrates an X-ray image generating method, in accordance with an exemplary embodiment.

FIG. 9 is a flowchart which illustrates an X-ray image generating method, in accordance with an exemplary embodiment.

With reference to FIG. 9, in operation 411, X-rays are generated and irradiated toward a target object, X-rays which have passed through the target object are detected in operation 412, and X-ray images based on different energy bands are acquired in operation 413. In another exemplary embodiment which will be described in detail below, X-ray images in which separation of materials is not performed are referred to as original images.

In order to acquire the original images based on different energy bands, X-rays of different energy bands may be irradiated plural times in operation 411, or wide band X-rays which include a plurality of energy bands may be irradiated one time in operation 411, and X-rays detected in operation 412 may be separated according to the respective energy bands. In case of the former, a general charge integration type X-ray detector may be used, and in case of the latter, a photon counting type X-ray detector (PCD) may be used. Further, in case of the former, although not shown in FIG. 9, after X-rays of a first energy band are irradiated and then detected, X-rays of a second energy band are irradiated. In this aspect, operation 411 and operation 412 are repeated until irradiation of X-rays is completed.

Thereafter, in operation 414, material images are separated from the original images by using different X-ray attenuation characteristics of respective materials which constitute the target object. In accordance with an exemplary embodiment, if two kinds of materials are desired to be separated, two original images which correspond to two respective energy bands are acquired in operation 413, and two calculations in which at least one of the two original images is multiplied by a weight and then subtraction is executed is carried out in operation 414, thereby separating two material images from the original images.

As one example, if the materials desired to be separated are bones and soft tissues, a soft tissue image may be acquired by multiplying the original image which corresponds to the low energy band (hereinafter, referred to as a low energy image) by a designated weight and then subtracting a resultant value from the original image which corresponds to the high energy band (hereinafter, referred to as a high energy image). As a result of this exemplary process, an image in which soft tissues are clearly seen without bones may be acquired.

Conversely, a bone image may be acquired by multiplying the high energy image by a designated weight and then subtracting a resultant value from the low energy image. As a result of this exemplary process, an image in which bones are clearly seen without soft tissues may be acquired.

Otherwise, a soft tissue image or a bone image may be acquired by respectively multiplying each of the low energy image and the high energy image by proper respective weights and then executing a respective subtraction to each.

Further, if the materials desired to be separated are lesion tissues and non-lesion tissues, or calcifying tissues and non-calcifying tissues, the above-described method may be applied. However, based on which region the target object corresponds to, a lesion tissue may be included in a calcifying tissue, or may be included in a non-calcifying tissue.

As another example, if the target object is a breast which includes soft tissues, and the materials desired to be separated are glandular tissues (referred to as parenchymal tissues) and adipose tissues, a glandular tissue image and an adipose tissue image may be acquired by respectively multiplying each of a low energy image and a high energy image by proper weights and then executing a respective subtraction to each.

As another example, if three or more kinds of materials are desired to be separated, three or more original images which correspond to three or more respective energy bands are acquired in operation 413, and three or more material images may be separated from the original images by multiplying the respective original images by proper weights and executing a respective subtraction to each. In more detail, if the target object is the breast, images of three or more kinds of materials which are selected from the group consisting of adipose tissues, parenchymal tissues, calcifying tissues and lesion tissues may be separated from the original images. The method of separating material images from original images by multiplying each of the original images by respective weights and then executing respective subtractions is only one exemplary method used in the present exemplary embodiment, and other methods than such a method may be used in order to perform a separation of material images.

Thereafter, in operation 415, different color channels are mapped to the separated material images. For example, if two kinds of materials are separated from original images, a first color channel is mapped to the first material image and a second color channel is mapped to the second material image, and if three kinds of materials are separated from original images, a first color channel is mapped to the first material image, a second color channel is mapped to the second material image, and a third color channel is mapped to the third material image. Such color mapping has been described in detail above with respect to the X-ray imaging apparatus 100, and a detailed description thereof will thus be omitted.

Further, if the material desired to be separated is lesion tissues, different colors may be mapped based on respective progress stages of the lesion tissues, so that a user may recognize the progress stage of the lesion tissues while observing an X-ray image. In more detail, a case in which the RGB color space is used will be exemplarily described. When a lesion tissue image is separated from an original image, a red channel is mapped to the lesion tissue image. In particular, different values of the red channel may be mapped to the lesion tissue image based on progress stages of the lesion tissues. In the RGB color space, each color channel may express a color with values of 0 to 255, and thus, as the lesion tissues progress, a higher value or lower value is mapped so that the progress stage of the lesion tissues may be recognized based on the color of the lesion tissues. Relations between the progress stages of lesion tissues and color channel values may be defined in advance.

The progress stage of the lesion tissues is estimated by a brightness value of either of the original images or the material images, and thus different values of the red channel may be mapped based on brightness values of the lesion tissues. For example, if cancer cells as lesion tissues are generated in soft tissues, the brightness value of the lesion tissues may be increased due to dehydration. Therefore, because, as the brightness value increases, it is estimated that the lesion tissues progress, as the brightness value increases, the progress stage of the lesion tissues may be expressed by mapping a higher red channel value or a lower red channel value.

Further, kinds or ratios of components which constitute the lesion tissues may be varied based on respective progress stages of the lesion tissues. Therefore, different colors may be mapped to the lesion tissues based on progress stages of the lesion tissues without consideration of the brightness value of the lesion tissues. In particular, a first color which is mapped to late-stage lesion tissues and a second color which is mapped to early-stage lesion tissues may be different.

The above description is only exemplary to represent the progress stage of lesion tissues, and the color space which is used or the color channel which is mapped to the lesion tissues are not limited thereto.

Thereafter, in operation 416, the material images to which different color channels are mapped are combined into one single image. In particular, the different color channels to which the material images are mapped are combined into one image.

Thereafter, in operation 417, brightness information is acquired from the X-ray images which are acquired in operation 413, and the brightness information is applied to the generated image. In more detail, one of the X-ray images based on different energy bands, i.e., the plurality of original images, may be selected, and brightness information which is included in the selected original image may be directly employed, a mean image with respect to the original images may be generated and brightness information which is included in the mean image may be employed, or brightness information which is included in a weighted sum image which is generated by computing a weighted sum of the original images may be employed. Because the original images, the mean image and the weighted sum image are all black and white images and represent brightness information, brightness information may refer to each image itself.

In particular, operation 417 may be executed such that a brightness image may be combined with the image which is generated by combining the plurality of material images to which different color channels are mapped, or that a brightness channel to which the brightness image is mapped may be combined with the image which is generated by combining the different color channels to which the plurality of material images are mapped. More particularly, the brightness channel may be a channel which substantially includes brightness information, such as, for example, a Y channel or an I channel, or one of color channels may be used as the brightness channel, such as, for example, mapping of brightness information to a G channel from among RGB channels.

Figure 10:
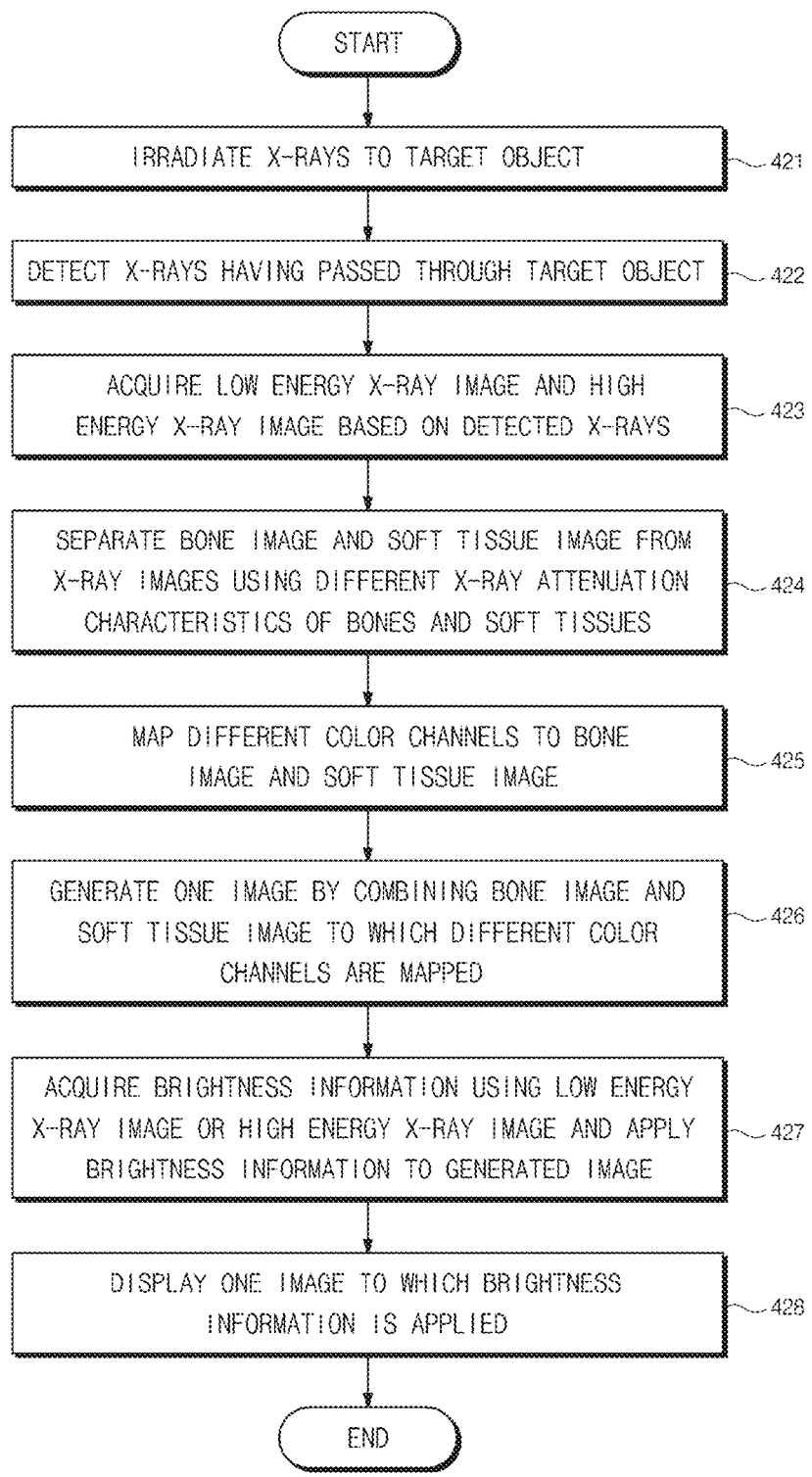
FIG. 10 is a flowchart which illustrates a separation of bones and soft tissues in an X-ray image generating method, in accordance with another exemplary embodiment.

Thereafter, in operation 418, the single image to which the brightness information is applied is displayed by using the display unit. In particular, if a color space which is used for performing a color mapping and a color space which is used by the display unit are different, the color channels of the image are converted into color channels which are expressible by the display unit, and then the image is displayed via the display unit. In the displayed image, different materials which constitute the target object are expressed in different colors, and thus a distinction between the materials may be improved, and a brightness of the original images is applied to the generated image, and thus artifacts may be reduced and the generated image may have excellent quality. FIG. 10 is a flowchart which illustrates a separation of bones and soft tissues in an X-ray image generating method, in accordance with another exemplary embodiment.

With reference to FIG. 10, in operation 421, X-rays are generated and irradiated toward a target object, and in operation 422, X-rays which have passed through the target object are detected. Thereafter, in operation 423, a low energy X-ray image and a high energy X-ray image are acquired based on the detected X-rays.

In order to acquire the X-ray image of the high energy band and the X-ray image of the low energy band, X-rays of the high energy band and X-rays of the low energy band may be respectively irradiated in operation 421, or wide band X-rays which include the high energy band and the low energy band may be irradiated in operation 421 and the detected X-rays may be separated into the high energy band and the low energy band in operation 422. If the target object is the chest, for example, an energy band which has a maximum energy of 140 keV may become the high energy band and an energy band which has a maximum energy of 70 keV may become the low energy band.

Thereafter, in operation 424, a bone image and a soft tissue image are respectively separated from the high energy image and the low energy image by using different X-ray attenuation characteristics of bones and soft tissues. In accordance with an exemplary embodiment, Dual-Energy X-ray Absorptiometry may be used.

Thereafter, in operation 425, different color channels are mapped to the separated bone image and soft tissue image. In particular, the color channels may be mapped using any one or more of various color spaces. For example, at least one of various color spaces, such as a YUV color space, an HSI color space, an HSV color space and an HSL color space in which color information and brightness information are separated, and a CMY color space, a CMYK color space and an RGB color space in which color information includes brightness information, may be used. Such color mapping has been described in detail above with respect to the X-ray imaging apparatus 100, and a detailed description thereof will thus be omitted.

Thereafter, in operation 426, the bone image and the soft tissue image to which the different color channels are mapped are combined into one single image. In particular, the color channel to which the bone image is mapped and the color channel to which the soft tissue image is mapped are combined into one single image.

Thereafter, in operation 427, brightness information is acquired by using the low energy X-ray image and the high energy X-ray image, and the brightness information is applied to the generated image. In more detail, one of the low energy original image and the high energy original image may be selected and brightness information which is included in the selected original image may be directly employed, a mean image with respect to the original images may be generated and brightness information which is included in the mean image may be employed, or brightness information which is included in a weighted sum image which is generated by computing a the weighted sum of the original images may be employed. Because the original images, the mean image and the weighted sum image are all black and white images and represent brightness information, brightness information may refer to each image itself.

Thereafter, in operation 428, the one single image to which the brightness information is applied is displayed by using the display unit. In the displayed image, the bones and soft tissues are expressed in different colors and thus distinction therebetween may be improved, and brightness information which is included in the original images is applied to the generated image and thus artifacts may be reduced and the generated image may have excellent quality.

Figure 11:
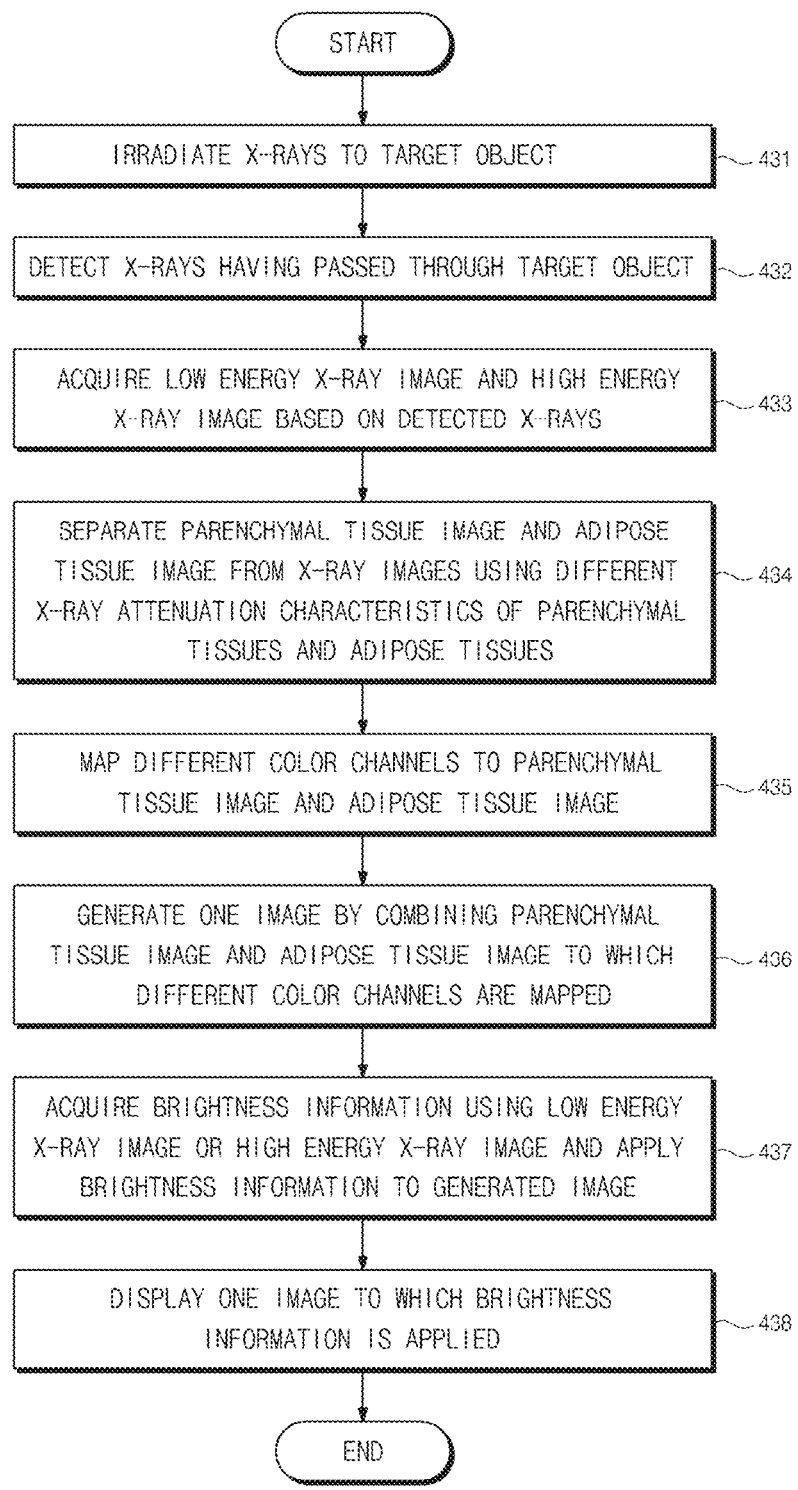
FIG. 11 is a flowchart which illustrates a separation of breast parenchymal tissues and soft tissues in an X-ray image generation method, in accordance with a further exemplary embodiment.

FIG. 11 is a flowchart which illustrates a separation of breast parenchymal tissues and soft tissues in an X-ray image generation method, in accordance with an exemplary embodiment.

First, in operation 431, X-rays are generated and irradiated toward a target object, and in operation 432, X-rays which have passed through the target object are detected. Because the target object is the breast, the target object may be photographed by using the X-ray imaging apparatus (i.e., a mammography apparatus), as shown in FIG. 1B. Thereafter, in operation 433, a low energy X-ray image and a high energy X-ray image are acquired based on the detected X-rays.

In order to acquire the X-ray image of the high energy band and the X-ray image of the low energy band, X-rays of the high energy band and X-rays of the low energy band may be respectively irradiated in operation 431, or wide band X-rays which include both of the high energy band and the low energy band may be irradiated in operation 431 and the detected X-rays may be separated into the high energy band and the low energy band in operation 432. Because the target object is the breast, an energy band which has a maximum energy of 30 keV may become the low energy band and an energy band which has a maximum energy of 50 keV may become the high energy band.

Thereafter, in operation 434, a parenchymal tissue image and an adipose tissue image are respectively separated from the high energy image and the low energy image by using different X-ray attenuation characteristics of parenchymal tissues and adipose tissues. In accordance with an exemplary embodiment, Dual-Energy X-ray Absorptiometry may be used. In particular, the parenchymal tissues are tissues which execute the actual function of the breast, and which refer to glandular tissues.

Thereafter, in operation 435, different color channels are mapped to each of the separated parenchymal tissue image and the adipose tissue image. In particular, the color channels may be mapped by using any one or more of various color spaces. For example, at least one of various color spaces, such as a YUV color space, an HSI color space, an HSV color space and an HSL color space in which color information and brightness information are separated, and a CMY color space, a CMYK color space and an RGB color space in which color information includes brightness information, may be used. Such color mapping has been described in detail above with respect to the X-ray imaging apparatus 100, and a detailed description thereof will thus be omitted.

Thereafter, in operation 436, the parenchymal tissue image and the adipose tissue image to which the different color channels are mapped are combined into one single image. In particular, the color channel to which the parenchymal tissue image is mapped and the color channel to which the adipose tissue image is mapped are combined into one image.

Thereafter, in operation 437, brightness information is acquired by using the low energy X-ray image and the high energy X-ray image, and the brightness information is applied to the generated image. In more detail, one of the low energy original image and the high energy original image may be selected and brightness information which is included in the selected original image may be directly employed, a mean image with respect to the original images may be generated and brightness information which is included in the mean image may be employed, or brightness information which is included in a weighted sum image which is generated by calculating a weighted sum of the original images may be employed. Because the original images, the mean image and the weighted sum image are all black and white images and represent brightness information, brightness information may refer to each image itself.

Thereafter, in operation 438, the one image to which the brightness information is applied is displayed by using the display unit. In the displayed image, parenchymal tissues and adipose tissues are expressed in different colors, and thus a distinction therebetween may be improved, and brightness information which is included in the original images is applied to the generated image, and thus artifacts may be reduced and the generated image may have excellent quality.

As is apparent from the above description, an X-ray imaging apparatus and an X-ray image generating method provide one image in which constituent materials of a target object are mapped to different colors, thus allowing a user to easily distinguish normal tissues from lesion tissues in the image.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. An X-ray imaging apparatus comprising:
an X-ray generator which is configured to generate X-rays and to irradiate the X-rays toward a target object;
an X-ray detector which is configured to acquire X-ray data which corresponds to a plurality of energy bands by detecting X-rays which have passed through the target object; and
a controller which is configured to: acquire a plurality of material images in which a plurality of materials which constitute the target object are respectively displayed and brightness information from the X-ray data, and generate a single image by mapping different color channels to each of the acquired plurality of material images and combining the plurality of material images into the single image, and apply the brightness information to the generated single image.

2. The X-ray imaging apparatus according to claim 1, wherein the controller includes an image acquisition unit which is configured to acquire original images which respectively correspond to each of the plurality of energy bands.

3. The X-ray imaging apparatus according to claim 2, wherein the controller further includes an image separation unit which is configured to separate the plurality of material images from the acquired original images based on the plurality of energy bands by using different X-ray attenuation characteristics of the plurality of materials.

4. The X-ray imaging apparatus according to claim 3, wherein the controller further includes a brightness information acquisition unit which is configured to acquire the brightness information from the acquired original images.

5. The X-ray imaging apparatus according to claim 4, wherein the brightness information acquisition unit is further configured to acquire the brightness information from one selected from among the acquired original images, a mean image from among the acquired original images, or a weighted sum image which is formed by weighting the acquired original images and then summing the weighted images.

6. The X-ray imaging apparatus according to claim 4, wherein the controller further includes a color mapping unit which is configured to map the different color channels to each of the separated plurality of material images.

7. The X-ray imaging apparatus according to claim 6, wherein the controller further includes an image combining unit which is configured to generate the single image by combining the plurality of material images to which the different color channels are mapped, and to apply the brightness information acquired by the brightness information acquisition unit to the generated single image.

8. The X-ray imaging apparatus according to claim 7, wherein the image combining unit is further configured to generate the single image by mapping the brightness information to a brightness channel and combining the color channels with the brightness channel.

9. The X-ray imaging apparatus according to claim 6, wherein the color channels belong to at least one color space from among a YUV color space, a YCbCr color space, an HSI color space, an HSV color space, an HSL color space, a CMY color space, a CMYK color space and an RGB color space.

10. The X-ray imaging apparatus according to claim 1, wherein the X-ray generator is further configured to generate X-rays, each of which is respectively associated with a corresponding one of the plurality of energy bands, and to irradiate the X-rays.

11. The X-ray imaging apparatus according to claim 1, wherein:
the X-ray generator is further configured to irradiate wide band X-rays toward the target object; and
the X-ray detector is further configured to detect X-rays which have passed through the target object and to separate the detected X-rays based on the plurality of energy bands.

12. An X-ray image generating method comprising:
irradiating X-rays toward a target object and detecting X-rays which have passed through the target object;
acquiring a plurality of material images in which a plurality of materials which constitute the target object are respectively displayed and brightness information from the detected X-rays;
mapping different color channels to each of the acquired plurality of material images; and
generating a single image by combining the plurality of material images to which the color channels are mapped and applying the acquired brightness information to a result of the combining.

13. The X-ray image generating method according to claim 12, wherein the acquiring the plurality of material images and the brightness information includes acquiring original images which respectively correspond to each of a plurality of energy bands from the detected X-rays.

14. The X-ray image generating method according to claim 13, wherein the acquiring the plurality of material images and the brightness information further includes separating the plurality of material images from the acquired original images by using different X-ray attenuation characteristics of the plurality of materials.

15. The X-ray image generating method according to claim 14, wherein the acquiring the plurality of material images and the brightness information further includes acquiring the brightness information from the acquired original images.

16. The X-ray image generating method according to claim 15, wherein the acquiring the brightness information includes acquiring the brightness information from one selected from among the acquired original images, a mean image of the acquired original images, and a weighted sum image which is formed by weighting the acquired original images and then summing the weighted images.

* * * * *